(12) United States Patent  
Leng et al.

(10) Patent No.: US 8,426,163 B2
(45) Date of Patent: *Apr. 23, 2013

(54) PRODUCTION OF LIPIDATED PROTEINS IN E. COLI

(75) Inventors: Chih-Hsiang Leng, Zhunan Town (TW);
Shih-Jen Liu, Zhunan Town (TW);
Hsin-Wei Chen, Zhunan Town (TW);
Pele Choi-Sing Chong, Zhunan Town (TW)

(73) Assignee: National Health Research Institutes, Zhunan Town, Miaoli County (TW)

( * ) Notice: Subject to any disclaimer, the term of this patent is extended or adjusted under 35 U.S.C. 154(b) by 192 days.

This patent is subject to a terminal disclaimer.

(21) Appl. No.: 12/329,026

(22) Filed: Dec. 5, 2008

(65) Prior Publication Data

US 2009/0176273 A1    Jul. 9, 2009

Related U.S. Application Data

(60) Provisional application No. 61/012,263, filed on Dec. 7, 2007.

(51) Int. Cl.
*C12P 21/06* (2006.01)

(52) U.S. Cl.
USPC ........................................ 435/69.1

(58) Field of Classification Search .......... None
See application file for complete search history.

(56) References Cited

U.S. PATENT DOCUMENTS

| | | |
|---|---|---|
| 4,745,069 A | 5/1988 | Mayne et al. |
| 5,942,236 A | 8/1999 | Lobet et al. |
| 6,013,258 A | 1/2000 | Urban et al. |
| 6,183,746 B1 | 2/2001 | Urban et al. |
| 6,361,966 B1 | 3/2002 | Walker et al. |
| 6,538,118 B1 | 3/2003 | Huebner et al. |
| 6,582,704 B2 | 6/2003 | Urban et al. |
| 6,936,263 B2 | 8/2005 | Revets et al. |
| 7,097,843 B2 | 8/2006 | Urban et al. |
| 7,235,243 B2 | 6/2007 | Becker et al. |
| 2005/0276813 A1 | 12/2005 | Muhlradt et al. |
| 2005/0281835 A1* | 12/2005 | Yang .................. 424/185.1 |
| 2009/0081253 A1 | 3/2009 | Hanon et al. |
| 2010/0303849 A1 | 12/2010 | Chen et al. |
| 2010/0322953 A1 | 12/2010 | Leng et al. |
| 2012/0041179 A1 | 2/2012 | Hsieh et al. |

FOREIGN PATENT DOCUMENTS

| | | |
|---|---|---|
| CA | 2183416 | 8/1995 |
| EP | 1612218 | 1/2006 |
| JP | 2008-113608 | 5/2008 |
| WO | 92/05248 | 4/1992 |
| WO | 92-16636 | 10/1992 |
| WO | 99/10375 | 3/1999 |
| WO | WO 99/57280 | 11/1999 |

(Continued)

OTHER PUBLICATIONS

*E. coli* genotypes (last viewed on Feb. 1, 2011).*

(Continued)

*Primary Examiner* — Alexander Kim
(74) *Attorney, Agent, or Firm* — Occhiuti Rohlicek & Tsao LLP (57) ABSTRACT

Production of a lipidated protein in an *E. coli* strain adapted to membrane protein expression.

6 Claims, 12 Drawing Sheets

MKKLLIAAMMAAALAACSQEAKQEVKEAVQAVESDVKDTAA
SAAESAASAVEEAKDQVKDAAADAKASAEEAVTEAKEAVTE
AKEAVTEAKEAVTEAAKDTLNKAADATQEAADKMKDAAKHH
HLEHHHHHH

FOREIGN PATENT DOCUMENTS

| WO | WO 0100790 | * | 1/2001 |
|---|---|---|---|
| WO | WO/01/29236 | * | 4/2001 |
| WO | 2004/052395 | | 6/2004 |
| WO | 2007/199896 | | 10/2007 |
| WO | 2008/079372 | | 7/2008 |
| WO | 2010/148496 | | 12/2010 |

OTHER PUBLICATIONS

Dumon-Seignovert et al., The toxicity of recombinant proteins in *Escherichia coli*: a comparison of overexpression in BL21(DE3), C41(DE3), and C43(DE3)., Protein Expression and Purification, vol. 37, Issue 1, Sep. 2004, pp. 203-206.*

Green et al., The e(P4) Outer membrane Protein of *Haemophilus influenzae*: biologic activity of Anti-e Serum and Cloning and Sequencing of the Structural Gene., Infection and Immunity, 1991, vol. 59, pp. 3191-3198.*

Rezwan et al., Lipoprotein synthesis in mycobacteria., Micribiology, Mar. 2007, vol. 153, pp. 652-658.*

Wikman et al., General strategies for efficient adjuvant incorporation of recombinant subunit immunogens., Vaccine (2005), vol. 23, pp. 2331-2335.*

Kamalakkannan et al., Bacterial lipid modification of proteins for novel protein engineering application, Protein Engineering, Design & Selection (2004), vol. 17, pp. 721-729.*

Legrain et al., "Production of Lipidated Meningococcal Transferrin Binding Protein 2 in *Escherichia coli*" Protein Expression and Purification 6:570-578 (1995).

De et al., "Purification and Characterization of *Streptococcis pneumoniae* palmitoylated and pneumococcal surface adhesion A expressed in *Escherichia coli*," Vaccine: 18: 1811-1821 (2000).

Cullen et al., "Construction and Evaluation of a Plasmid Vector for the Expression of Recombinant Lipoproteins in *Escherichia coli*," Plasmid 49: 18-29 (2003).

Kamalakkannan et al., "Bacterial Lipid Modification of Proteins for Novel Protein Engineering Applications," Protein, Engineering, Design & Selection 17(10): 721-729 (2004).

Esche, U. v.d. et al. Immunostimulation by bacterial components: I. Activation of macrophages and enhancement of genetic immunization by the lipopeptide P3CSK4. Intl. 1. Immunopharm. Dec. 2000. vol. 22, pp. 1093-1102.

Hsu, C-A. et at. Immunoproteomic identification of the hypothetical protein NMB1468 as a novel lipoprotein ubiquitous in *Neisseria meningitidis* with vaccine potential. Proteomics. 2008. vol. 8, pp. 2115-2125.

Liu, et al. "Structure of the Human Papillomavirus E7 Oncoprotein and its Mechanism for Inactivation ofthe Retinoblastoma Tumor Suppressor", 1. Biol. Chem., Jan. 2006. vol. 281, pp. 578-586.

Steller et al. "Cell-mediated Immunological Responses in Cervical and Vaginal Cancer Patients Immunized with a Lipidated Epitope of Human Papillomavirus Type 16 E7." Clinical Cancer Research, vol. 4, Sep. 1998. pp. 2103-2109.

Sung, et al. Biochemical characterizations of *Escherichia coli*-expressed protective antigen Ag473 of *Neisseria meningitides* group B., Vaccine. vol. 28(51) Nov. 29, 2010, pp. 8175-8182.

ExPASy—PeptideCutter http://web.expasy.ort/cgi-bin/peptide_cutter/peptidecutter.pl (Accessed Mar. 7, 2012).

Shu, et al. Core Structure of the Outer membrane Lipoprotein from *Escherichia coli* at 1.9A Resolution, (2000) vol. 299, pp. 1101-11112.

Cote-Sierra, et al. "A New Membrane-Bound Oprl Lipoprotien Expression Vector High Prodcution of Heterologous Fusion Proteins in Gram (−) Bacteria and the Implications for Oral Vaccination" *Gene* (1998) vol. 221, pp. 25-34.

Crill, Wayne D., et al. "Monoclonal Antibodies That Blind to Domain III of Dengue Virus E Glycoprotien Are the Most Efficient Blockers of Virus Adsorption to Vero Cells" *Journal of Virology* (Aug. 2001) pp. 7769-7773.

Jackson, D.C., et al. "A totally synthetic vaccine of generic structure that targets Toll-like receptor 2 on dendritic cells and promotes antibody or cytotoxic T cell responses" *Proc. Natl. Acad. Sci. USA* vol. 101, No. 43 (2004) pp. 1540-15445.

Vieira et al., "A novel leptospiral protein increases ICAM-1 and E-selectin expression in human umbilical vein endothelial cells," FEMS Microbiol Lett 276: 172-180 (2007).

Whalan et al., "PiuA and PiaA, iron uptake lipoproteins of *Streptococcus pneumonia*, elicit serotype independent antibody response following human pneumococcal septicaemia," FEMS Immunology and Medical Microbiology, 43:73-80 (2005).

* cited by examiner

MKKLLIAAMMAAALAACSQEAKQEVKEAVQAVESDVKDTAA
SAAESAASAVEEAKDQVKDAAADAKASAEEAVTEAKEAVTE
AKEAVTEAKEAVTEAAKDTLNKAADATQEAADKMKDAAKHH
HLEHHHHHH

SEQUENCE LISTING

<160> NUMBER OF SEQ ID NOS: 10

<210> SEQ ID NO 1
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Asp Gln Val Lys Asp Ala Ala Ala Asp
    50                  55                  60

Ala Lys Ala Ser Ala Glu Glu Val Thr Glu Ala Lys Glu Ala Val
65                  70                  75                  80

Thr Glu Ala Lys Glu Ala Val Thr Glu Ala Lys Glu Ala Val Thr Glu
                85                  90                  95

Ala Ala Lys Asp Thr Leu Asn Lys Ala Ala Asp Ala Thr Gln Glu Ala
            100                 105                 110

Ala Asp Lys Met Lys Asp Ala Ala Lys His His Leu Glu His His
            115                 120                 125

His His His His
        130

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His His His Leu Glu His His His His His
1               5                   10

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaattccat atgaaaaaat tattgattgc                                    30

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgctcgagg tgatgatgtt tggcggcatc tttcattttg                    40

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Lys Lys Leu Leu Ile Ala Ala Met Met Ala Ala Ala Leu Ala Ala
1               5                   10                  15

Cys Ser Gln Glu Ala Lys Gln Glu Val Lys
            20                  25

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Lys Lys Leu
1

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Ser Gln Glu Ala Lys Gln Glu Val Lys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gln Glu Ala Lys Gln Glu Val Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Ser Gln Glu Ala Lys
1               5

<210> SEQ ID NO 10
<211> LENGTH: 4
<212> TYPE: PRT
<213> ORGANISM: Artificial sequence

```
<220> FEATURE:
<223> OTHER INFORMATION: Synthetic peptide
<220> FEATURE:
<221> NAME/KEY: Variant
<222> LOCATION: (1)..(1)
<223> OTHER INFORMATION: Leu, Val, or Ile
<220> FEATURE:
<221> NAME/KEY: Variant
<222> LOCATION: (2)..(2)
<223> OTHER INFORMATION: Ala, Ser, Thr, Val, or Ile
<220> FEATURE:
<221> NAME/KEY: Variant
<222> LOCATION: (3)..(3)
<223> OTHER INFORMATION: Gly, Ala, or Ser

<400> SEQUENCE: 10

Xaa Xaa Xaa Cys
1
```

PRODUCTION OF LIPIDATED PROTEINS IN E. COLI

CROSS-REFERENCE TO RELATED APPLICATION

This application claims the benefit of U.S. Provisional Application 61/012,263, filed Dec. 7, 2007, the content of which is incorporated herein by reference in its entirety.

BACKGROUND OF THE INVENTION

Vaccination is considered to be the most effective and efficient approach to prevent pathogen infection. A vaccine contains a pathogen-derived antigenic material (e.g., protein) for inducing protective immune responses. Modified proteins, e.g., lipidated proteins, are more antigenic than unmodified proteins.

Proteins used for vaccine preparation are commonly made by recombinant technology, e.g., expressed in E. coli. However, E. coli is generally viewed as not suitable for producing modified proteins, particularly, lipidated proteins, as it either does not lipidate proteins, or lipidate proteins poorly.

SUMMARY OF THE INVENTION

The present invention is based on the unexpected discovery that C41(DE3) and C43(DE3), two E. coli mutants capable of overly expressing membrane proteins, produced Ag473, a protein of Neisseria Mengitidis, with a high level of lipidation.

Accordingly, this invention provides a method of producing a lipidated protein in an E. coli strain adapted to membrane protein expression, such as C41(DE3) and C43(DE3). This method includes two steps: (i) providing the just-mentioned E. coli strain transformed with an expression plasmid including a nucleotide sequence that encodes a naturally lipidated protein (e.g., a Braun lipoprotein), and (ii) culturing the transformed E. coli strain to allow expression of the protein in lipidated form. Alternatively, this method includes two additional steps following the culturing step: (iii) isolating the protein thus expressed and (iv) confirming that the protein is lipidated. The term "naturally lipidated protein" refers to a protein that is in lipidated form when produced in its natural source.

The details of one or more embodiments of the invention are set forth in the description below. Other features or advantages of the present invention will be apparent from the following drawings and detailed description of one example, and also from the appended claims.

BRIEF DESCRIPTION OF THE DRAWINGS

The drawings are first described.

DETAILED DESCRIPTION OF THE INVENTION

Described herein is a method of producing lipidated proteins in E. coli, in particular, in E. coli strains that are adapted to membrane protein expression.

The E. coli strains used in the method of this invention are resistant to the toxic effects induced by over-expression of exogenous proteins, in particular, membrane proteins. Such E. coli strains can be identified/generated by the methods described in U.S. Pat. No. 6,361,966. Examples of these E. coli strains include, but are not limited to, C43(DE3) (ECCC B96070445), C41(DE3) (ECCC B96070444), C0214(DE3), DK8(DE3)S (NCIMB 40885), and C2014(DE3) (NCIMB 40884).

Any of the *E. coli* strains mentioned above can be used to produce a natural lipoprotein in lipidated form. A natural lipoprotein or lipidated protein is a protein that is lipidated in its native state. In one example, the natural lipoprotein is a mycobacterial lipoprotein, e.g., a Braun lipoprotein. Braun lipoprotein is a family of bacterial proteins having a N-acyl-5-diacylglyceryl moiety attached to a Cys residue. See Madan et al., Bioinformatics 18:641-643. All Braun lipoproteins include a lipobox that includes the consensus amino acid sequence [LVI][ASTVI][GAS][C] (SEQ ID NO: 10). See von Heijne et al., Protein Eng 2:531-534, 1989; Hayashi et al., J. Bioenerg. Biomembr 22:451-471, 1990. Exemplary Braun lipoproteins are listed in DOLOP, a database of bacterial lipoproteins (www.mrc-lmb.cam.ac.uk/genomes/dolop) and also in the attached Appendix. Other Braun lipoproteins can be identified based on their amino acid sequences using the lipoprotein-predicting software also provided in the DOLOP database. See www.mrc-lmb.cam.ac.uk/genomes/dolop/analysis.shtml.

A natural lipoprotein can be expressed in one of the *E. coli* strains noted above via conventional recombinant technology. Briefly, a DNA fragment encoding a natural lipoprotein is obtained from its native source via, e.g., PCR amplification, and optionally modified to optimize codon usage in *E. coli*. The DNA fragment is then inserted into an *E. coli* expression vector to produce an expression plasmid. Preferably, expression of the lipoprotein is driven by a strong promoter, e.g., T7, T5, T3, or SP6, which can be inducible, e.g., by IPTG. The expression plasmid is then introduced into a selected *E. coli* strain and positive transformants are cultured under suitable conditions for protein expression. The lipoprotein thus expressed can be isolated from the *E. coli* cells and its lipidation status can be confirmed via methods known in the art, e.g., immunoblotting with an anti-lipoprotein antibody or mass spectrometry.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

Expression of rAg473 in C43(DE3) and Characterization Thereof (a) Construction of pET22b_Ag472_9His Expression Plasmid Based on the gene sequence of Ag473 (*Neisseria Mengitidis*) disclosed under GenBank accession no. AY35098 (Sep. 1, 2005), a DNA fragment encoding Ag473 was obtained via polymerase chain reaction using the primers of:

Forward primer (containing an Nde I site): 5'-GGAATTC-CATATGAAAAAATTATTG AT TGC-3' (SEQ ID NO:3), Reverse primer (containing an XhoI site): 5'CCGCTC-GAGGTGATGATGTTTGGCG GCATCTTTCATTTTG-3' (SEQ ID NO:4).

Compared to the native Ag473 protein, the polypeptide encoded by the amplified DNA fragment contains three extra His residues at the C-terminus.

This DNA fragment was cloned into expression vector pET-22b(+) (Novagen, Madison, Wis.) via the Nde I and Xho I sites to generate expression plasmid pET22b_Ag473_9His (see FIG. 1). The recombinant Ag473 (rAg473) expressed from this plasmid contains a C-terminal tag of HHHLEHH-HHHH (SEQ ID NO:2). See FIG. 1B.

(b) Expression of rAg473 in Various *E. coli* Strains

Expression plasmid pET22b_Ag473_9H is was introduced into three *E. coli* strains, i.e., JM109 (DE3), (a K strain, Promega, Madison, Wis.), BL21(DE3) (a B strain, Novagen, Madison, Wis.), and C43(DE3) (Imaxio, Saint-Beauzire, France). The transformants thus obtained were cultured at 37° C. overnight and the expression of rAg473 was then induced with 0.5 mM of IPTG. The cells were further cultured for an additional 3 hours and then harvested by centrifugation (8000×g for 20 min). The cell pellets, re-suspended in 100 ml of a homogenate buffer (20 mM Tris-Cl (pH 8.0), 500 mM NaCl, 10% glycerol, 50 mM sucrose, and 10 mM imidazole), with or without Triton-100, were disrupted with a French Press (Constant Systems, Daventry, UK) at 27 Kpsi. The resultant cell lysates were centrifuged at 80,000×g for 60 min and the supernatants thus obtained were collected.

Figure 1A:
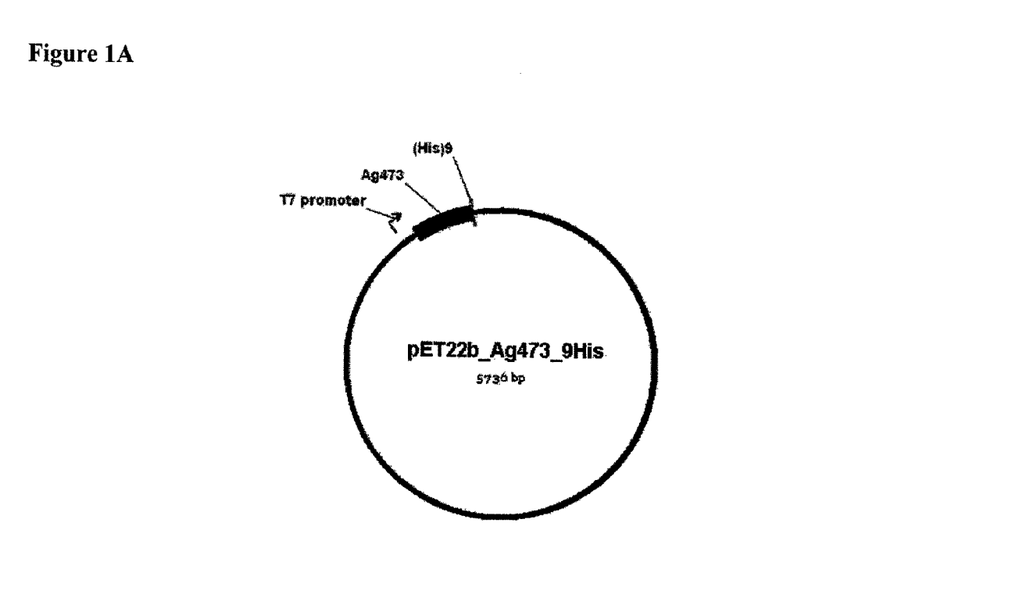
FIG. 1A is a map of expression plasmid pET22b_Ag473_9His.
Figure 1B:
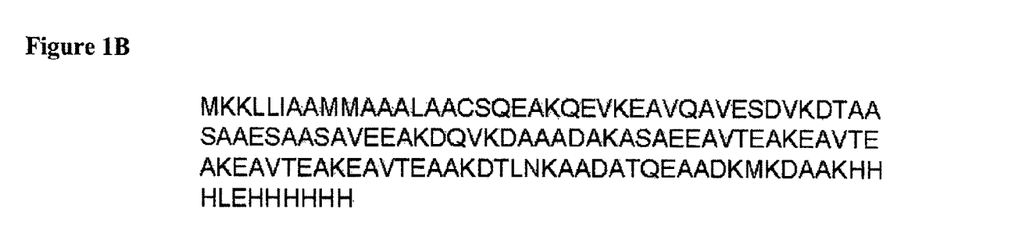
FIG. 1B is the amino acid sequence (SEQ ID NO:1) of the recombinant Ag473 (rAg473) expressed from pET22b_Ag473_9H is. Compared to the amino acid sequence of the native Ag473 protein (GenBank accession no. AY566590.1, GI:49616841, Apr. 1, 2005), rAg473 includes a C-terminal tag of HHHLEHHHHHH (SEQ ID NO:2).
Figure 1C:
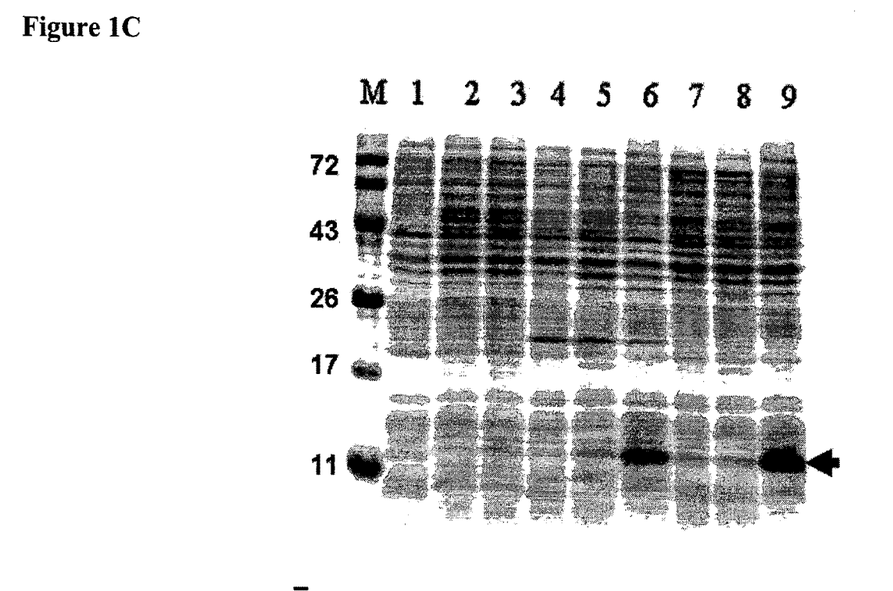
FIG. 1C is a photo of a polyacrylamide gel stained with Coomassie Brilliant Blue R-250, showing the expression of rAg473 in JM109(DE3), BL21(DE3), and C43(DE3). M: molecular weight markers; Lanes 1, 4, and 7: proteins isolated from untransformed JM109(DE3), BL21(DE3), and C43(DE3) cells, respectively; Lane 2, 5, and 8: proteins isolated from JM109(DE3), BL21(DE3), and C43(DE3) transformed with pET22b_Ag473_9His, respectively; and Lane 3, 6, and 9: proteins isolated from JM109(DE3), BL21(DE3), and C43(DE3) transformed with pET22b_Ag473_9His and induced with isopropyl β-D-thiogalactoside (IPTG). The arrow indicates the position of the rAg473 protein on the gel.
Figure 1D:
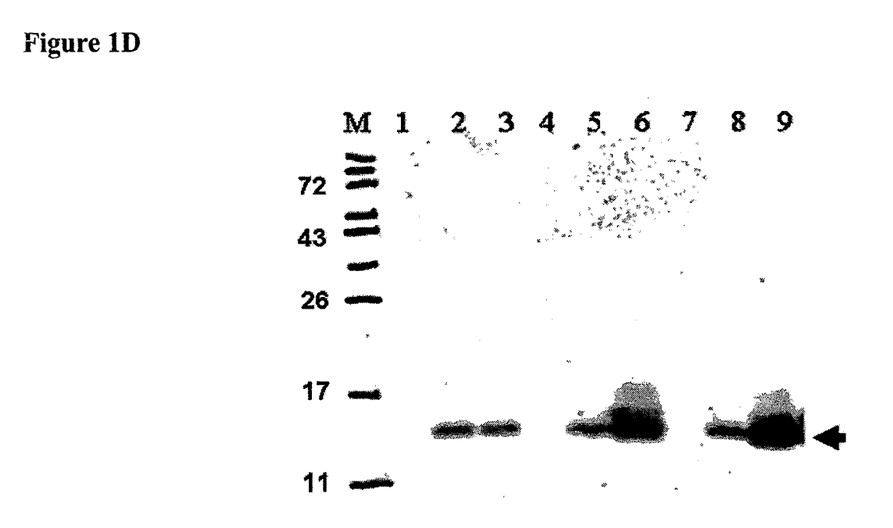
FIG. 1D is a photo showing that the rAg473 protein expressed in BL21(DE3) and C43(DE3) is reactive to both anti-His tag and anti-Ag473 antibodies.

The presence of rAg473 in the supernatants was first examined by SDS-PAGE analysis. Briefly, 10 µl of each supernatant was mixed with an equal volume of a sample buffer (63 mM Tris-HCl (pH 6.8), 2% SDS, 5% 2-mercaptoethanol, 10% glycerol, and 0.002% bromophenol blue) and heated in boiling water for 3 min. The mixture was then loaded (5~50 µg protein per lane) on a 15% SDS-Polyacrylamide gel and subjected to electrophoresis. Proteins, separated on the gel, were then stained with Coomassie Brilliant Blue R-250. As shown in FIG. 1C, the expression of rAg473 in JM109(DE3) was not detected. In contrast, more than 10% of the total proteins expressed in BL21(DE3) and C43(DE3) were rAg473.

The rAg473 expressed in the three *E. coli* strains was further verified by immunoblotting. The proteins separated on the SDS-polyacrylamide gel were transferred electrophoretically to a polyvinylidene difluoride (PVDF) membrane (Millipore, Billerica, Mass., USA) at 392 mA for 40 min. The membrane was then blocked overnight at 4° C. with PBS containing 5% non-fat milk and 0.05% Tween-20. After being washed with PBS containing 0.05% Tween-20 (PBST), the membrane was incubated with a mouse anti-His antibody (1:1500 dilution, Amersham Biosciences, New Territories, HK), or an anti-Ag473 antibody at room temperature for 1 h and then washed multiple times with PBST. Afterwards, the membrane was incubated with a horseradish peroxidase (HRP)-conjugated goat anti-mouse IgG antibody (1:5000, Bethyl Laboratories, Montgomery, Tex., USA) for 1 h, washed multiple times with PBST, and signals were developed in 0.2 mM 3,3'-diaminobenzidine tetrahydrochloride (Sigma, St. Louis, Mo., USA) for 2~3 min. The membrane was then washed with distilled water to stop signal development.

Results obtained from the immunoblotting assay echo those obtained from SDS-PAGE analysis, i.e., rAg473 was expressed in BL21(DE3) and C43(DE3) at high levels while its expression in JM09(DE3) was not detected.

(c) Purification of rAg473

Each of the rAg473-containing supernatants mentioned in section (b) above was loaded on a column (2.2 cm i.d.×5.3 cm) containing 20 ml of Ni-NTA resin (Qiagen, San Diego, Calif., USA). The column was washed with the homogenate buffer and balanced with the same buffer containing 50 mM imidazole. rAg473 was eluted with the homogenate buffer contained 500 mM imidazole and examined by SDS-PAGE analysis and immunoblotting.

Figure 2:
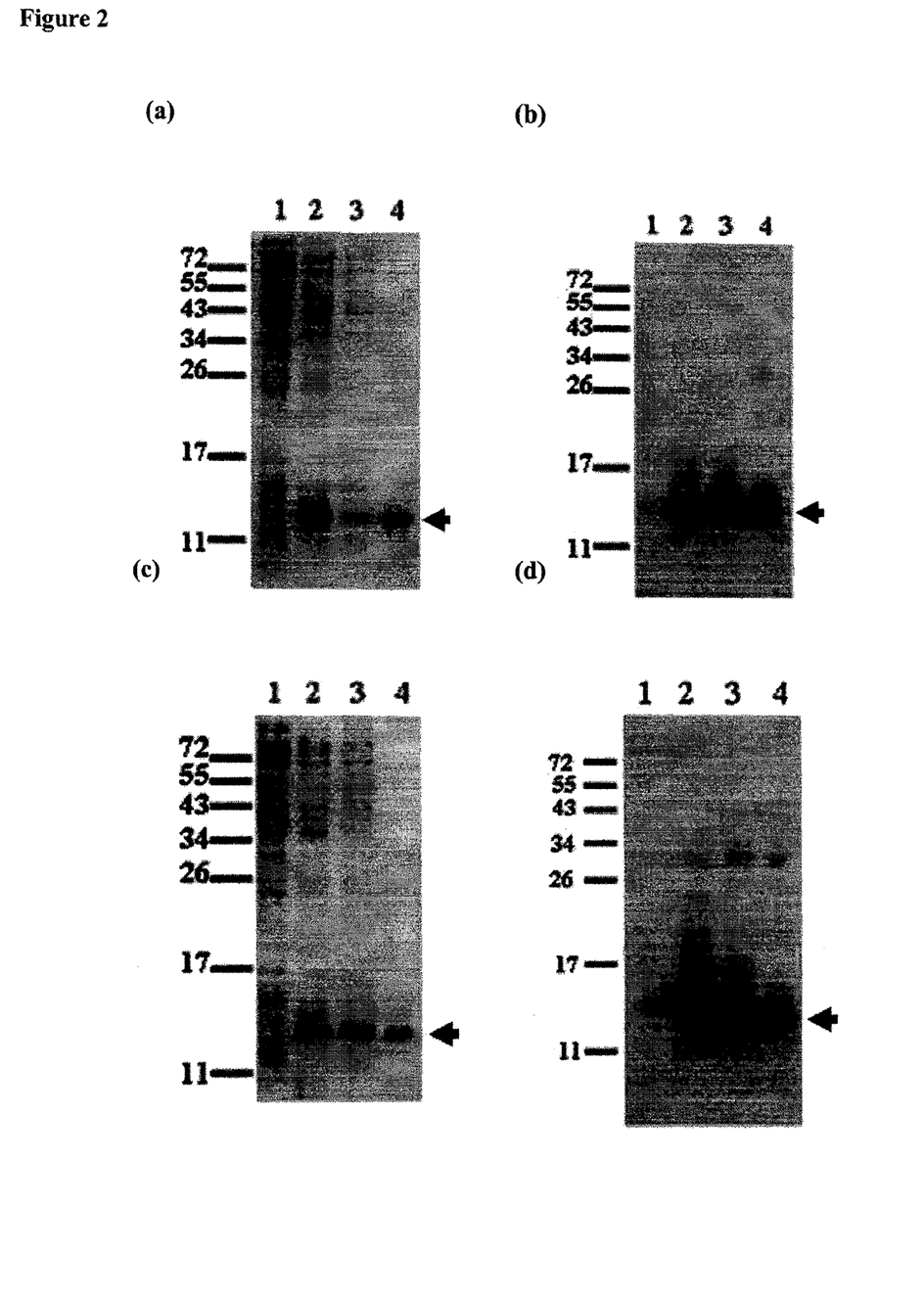
FIG. 2 is a number of photos showing purified rAg473 proteins on polyacrylamide gels stained with Coomassie Brilliant Blue R-250. The arrow in each panel below indicates the position of the rAg473 protein. Panel (a): 15% reduced SDS-PAGE gel stained with Coomassie blue. Lanes 1-4 were loaded respectively with lysate of cells not induced by IPTG, lysate of cells induced by IPTG, a detergent-free soluble fraction obtained from the IPTG-induced cells, and purified rAg473. Panel (b): immunoblotting of the purified rAg473 protein. Panel (c): 15% reduced SDS-PAGE gel stained with Coomassie. Lanes 1-4 were loaded respectively with lysate of cells not induced by IPTG, lysate of cells induced by IPTG, a detergent-containing soluble fraction obtained from the IPTG-induced cells, and purified rAg473.

As shown in FIG. 2, rAg473 was isolated from C43(DE3) via the just-described method with high purity. The results also indicate that addition of Triton-100 when disrupting *E. coli* cells increased protein yields. See FIGS. 2(c) and 2(d) as compared to FIGS. 2(a) and 2(b).

(d) Characterization of rAg473

(i) Determination of N-Terminal Residues by Edman Degradation

The rAg473 proteins purified from C43(DE3) and BL21 (DE3) as described above were dialyzed against 5 mM ammonia bicarbonate and subjected to four cycles of Edman degradation using an Applied Biosystems Model 494 Procise Protein sequencer.

The N-terminal residues of the rAg473 protein isolated from BL21(DE3) were determined to be MKKL (SEQ ID NO:6), indicating that it has the N-terminal of a native Ag473 protein. The N-terminal amino acid residues of the rAg473 protein expressed in C43(DE3) could not be determined by this assay, suggesting that the N-terminus of the rAg473 protein was blocked by modification. This protein was subjected to further analysis as described below.

(ii) Modification of rAg473

Figure 3:
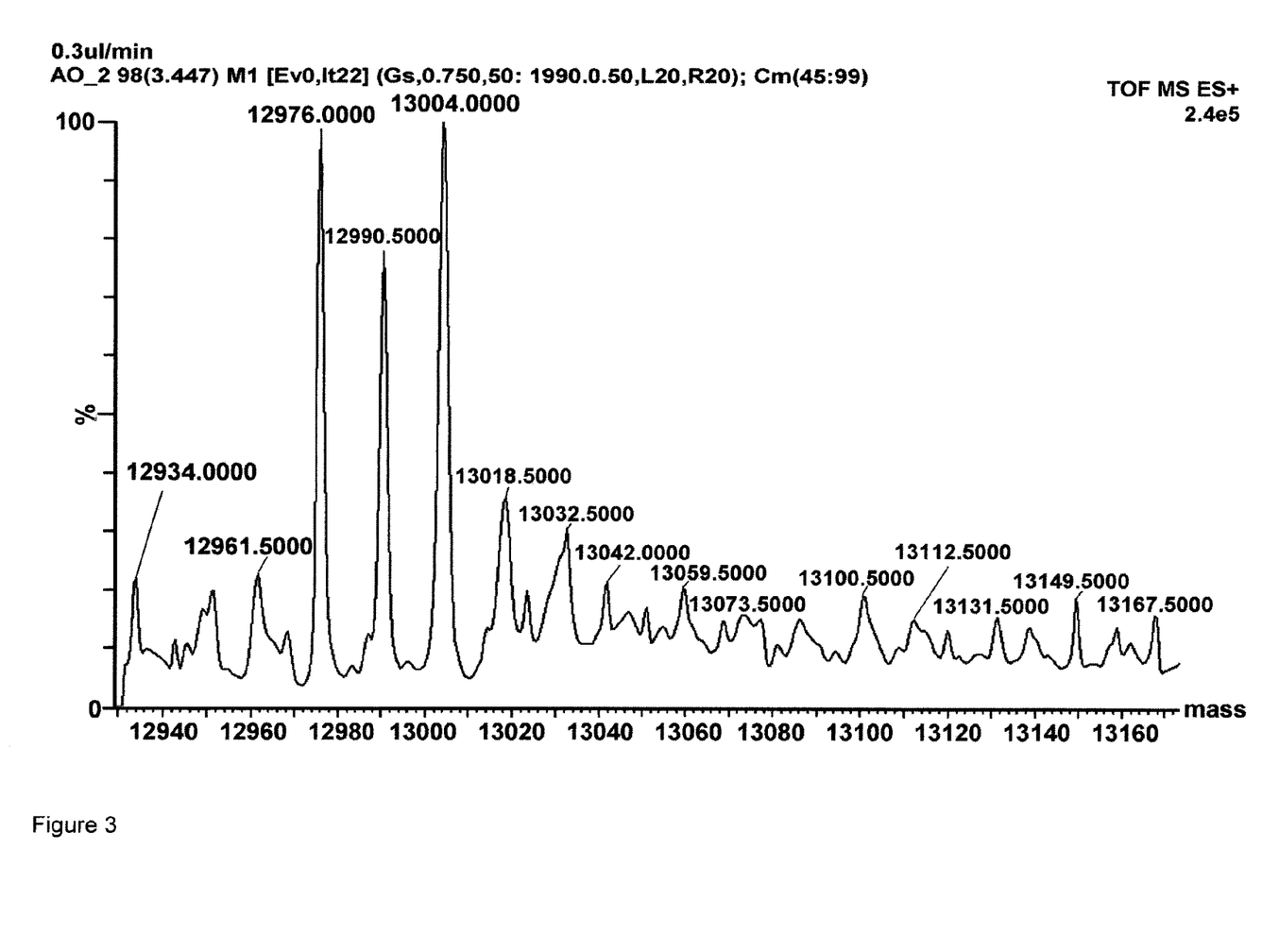
FIG. 3 is a liquid chromatography-mass spectrometry (LC/MS) graph showing that the rAg473 protein expressed in C43(DE3) cells had at least three subpopulations represented by peaks 12976, 12990, and 13004.

Intact rAg473, purified in the absence of Triton-100, was analyzed by LC/MS. The protein was infused into a Waters® ESI Quadrupole Time-of-Flight (Q-TOF) premier mass spectrometer following the manufacturer's instructions. The molecular mass of the rAg473 protein was calculated by the maximum entropy algorithm (MaxEnt, Waters) for 30 iterations. As show in FIG. 3, at least three peaks were detected, which differ from each other by 14 amu. This result indicates that the rAg473 protein includes at least three subpopulations, each having a distinct variation (i.e., a mutation in amino acid sequence or a modification on an amino acid residue).

(iii) Modification Type/Site of rAg473

The dialyzed rAg473 described above was digested by trypsin (Promega Co., Madison, Wis.) at a ratio of 50:1 (wt/wt) for two hours at room temperature. The digestion was terminated by addition of formic acid (1.2%) and the peptides thus yielded were analyzed by a matrix-assisted laser desorption ionization time-of-flight (MALDI-TOF) mass spectrometer (Burker). Briefly, 1 µl of the peptide sample was mixed with 1 µl of a saturated solution of α-ciano-4-hydrozycinnamic acid (Sigma) in acetonitrile/0.1% trifluoroacetic acid (1:3, vol/vol). One microliter of the mixture was placed on the target plate of the spectrometer for analysis.

Figure 4A:
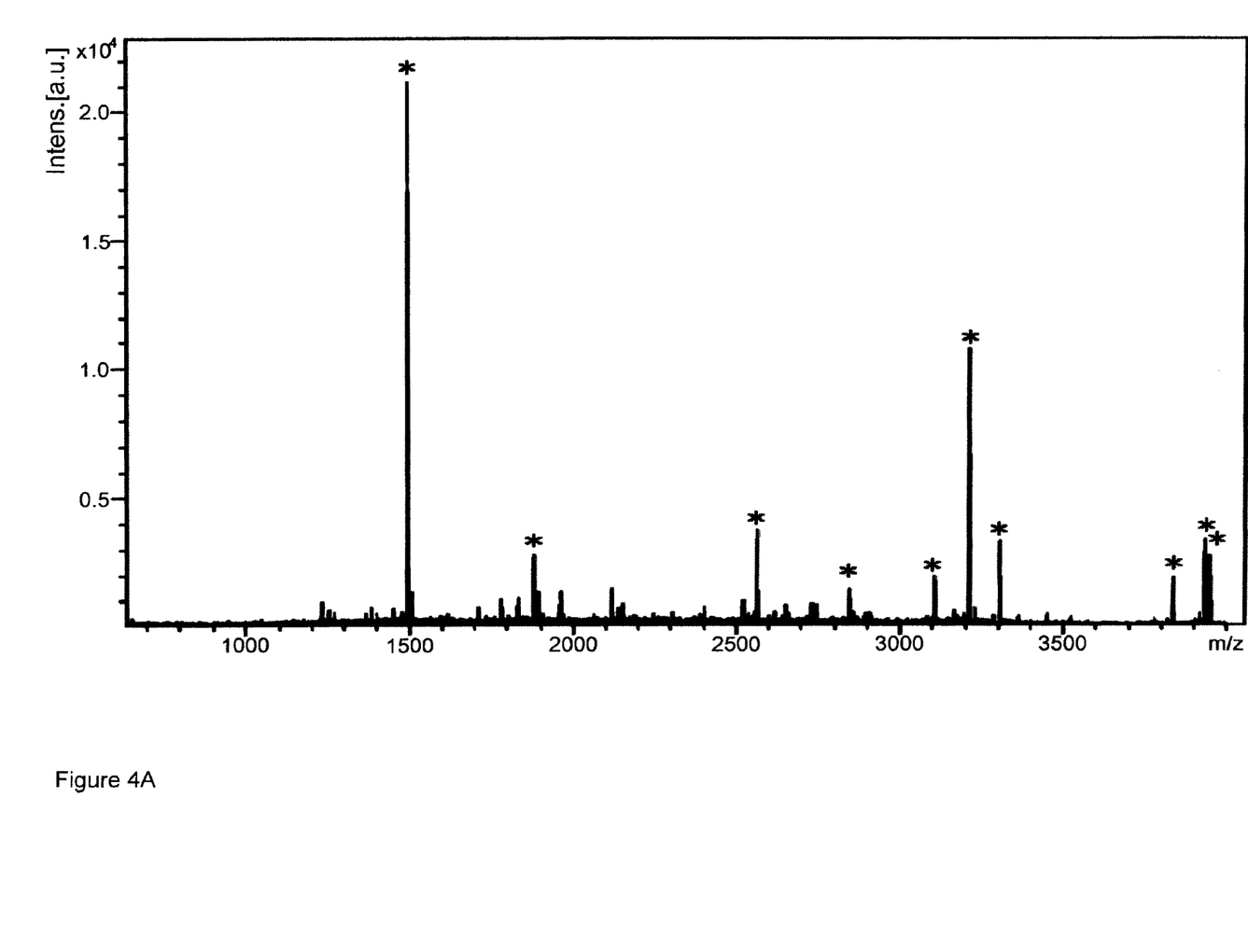
FIG. 4A is a matrix-assisted laser desorption ionization time-of-flight (MALDI-TOF) MS graph of the peptides derived from trypsin-digested rAg473 expressed in C43 (DE3).
Figure 4B:
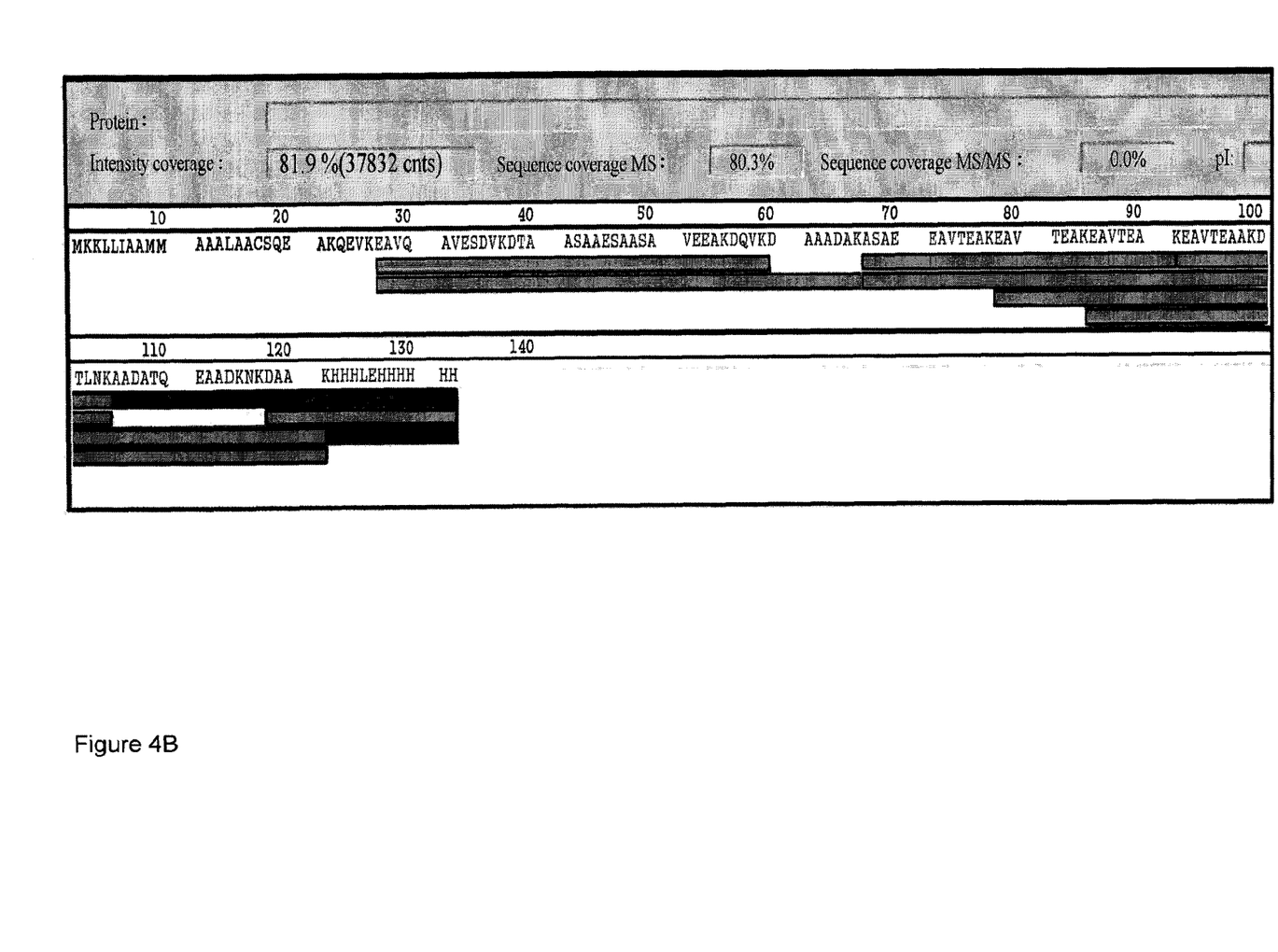
FIG. 4B is a diagram showing that the peaks shown in FIG. 4A represent fragments derived from the C-terminal region (residues 27-137) of the rAg473 protein expressed in C43 (DE3) (SEQ ID NO:1).

The major peptides produced in trypsin digestion corresponded to the C-terminal fragments of rAg473 (covering residues 27-132 of the Ag473 protein as determined by Burker's biotool software). See FIGS. 4A and 4B. Comparing with the data mentioned in section (ii) above, it is indicated that the variations found in the rAg473 protein are not located in the C-terminal fragments of the protein.

To generate peptides corresponding to the N-terminal fragments of rAg473, the protein was partially digested by trypsin for 10 minutes at room temperature (protein/enzyme: 50/1). The digested product was analyzed by a Waters® MALDI micro MX™ mass spectrometer as follows. One µl of the digested product was mixed with 1 µl of a saturated solution of α-ciano-4-hydrozycinnamic acid (Sigma) in acetonitrile/0.1% trifluoroacetic acid (1:3, vol/vol). One microliter of the mixture was placed on the target plate of the spectrometer for analysis.

Figure 5A:
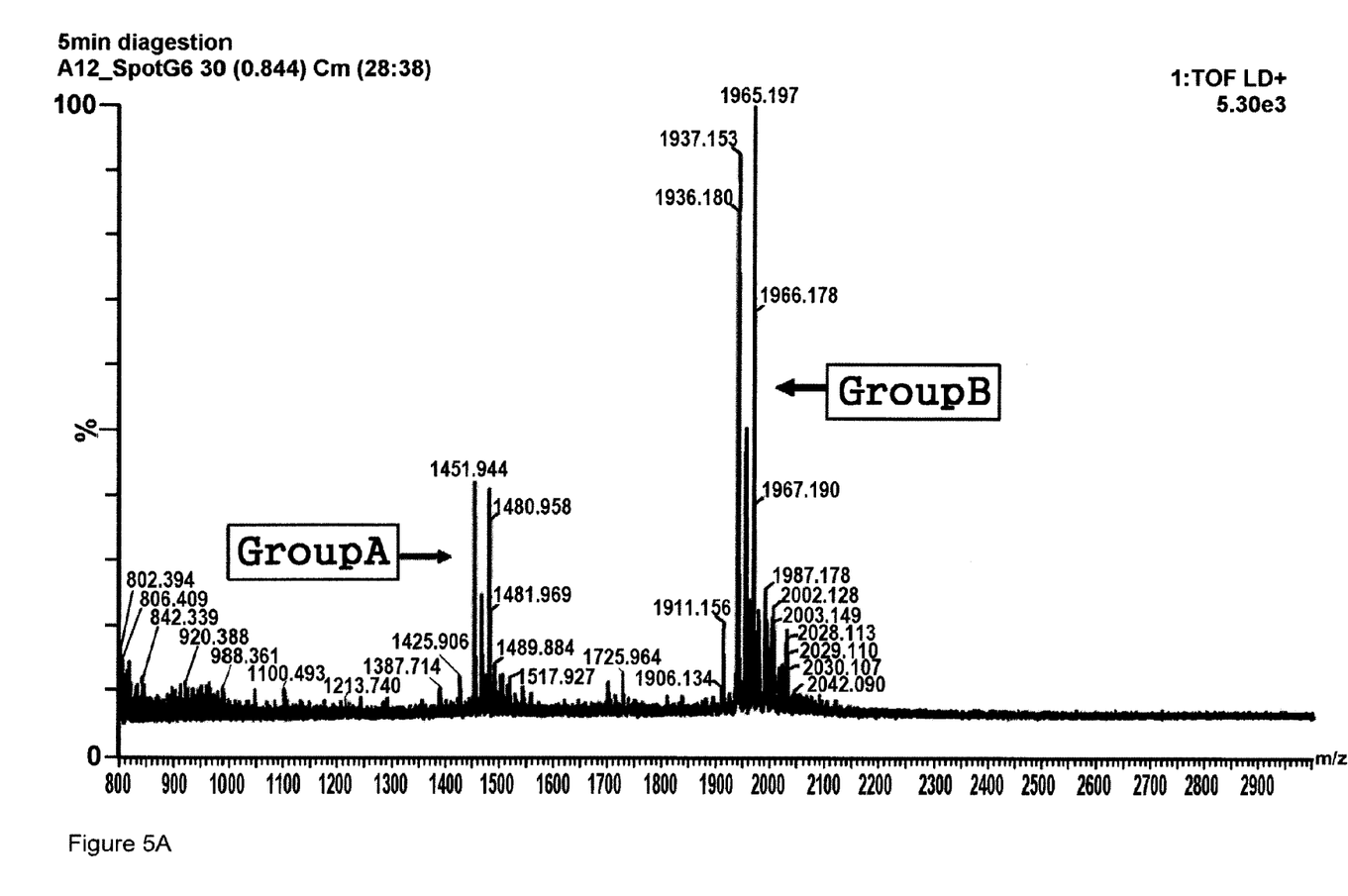
FIG. 5A is a MALDI-TOF MS graph showing that partial typsin digestion generates N-terminal fragments of rAg473, as represented Group A peaks and Group B peaks.

As shown in FIG. 5A, two major groups of peaks, Group A and Group B, were identified in this analysis. Group A includes three peaks at m/z 1451.9, 1465.9, and 1479.9 and Group B includes three peaks at m/z 1936.2, 1950.2, and 1964.2. The molecular mass of the peptide represented by each peak was determined. None of them corresponded to the N-terminal tryptic fragment of the unmodified Ag473 protein, i.e., MKKLLIAAMMAAALAACSQEA KQEVK (SEQ ID NO: 5). This result suggests that the N-terminal tryptic fragments of the rAg473 expressed in C43(DE3) contain variations.

To determine whether the variations were caused by mutations in the amino acid sequence or by protein modifications, the typsin-digested (10 min) rAg473 peptides were analyzed by Q-TOF mass spectrometry. The digested peptides were infused into a Waters® Q-TOF premier mass spectrometer following the manufacturer's instructions for MS and MS/MS modes. The peaks at m/z 968.6 and 975.6 shown in the MS mode were selected for MS/MS analysis. These two peaks correspond to the peaks at m/z 1936.2 and 1950.2 in Group B. See FIG. 5C. To synchronize the operation of the T-Wave™ collision cell in the MS/MS mode, the capillary voltage was set at 1800 V and the counter electrode was set at 40 V. Low-energy CID was performed using argon as a collision gas (pressure in the collision cell was set at $3\text{-}4\times10^{-5}$ mbar) and the collision energy was optimized manually for all precursor ions (in the range of 25 to 35 eV).

Figure 6A:
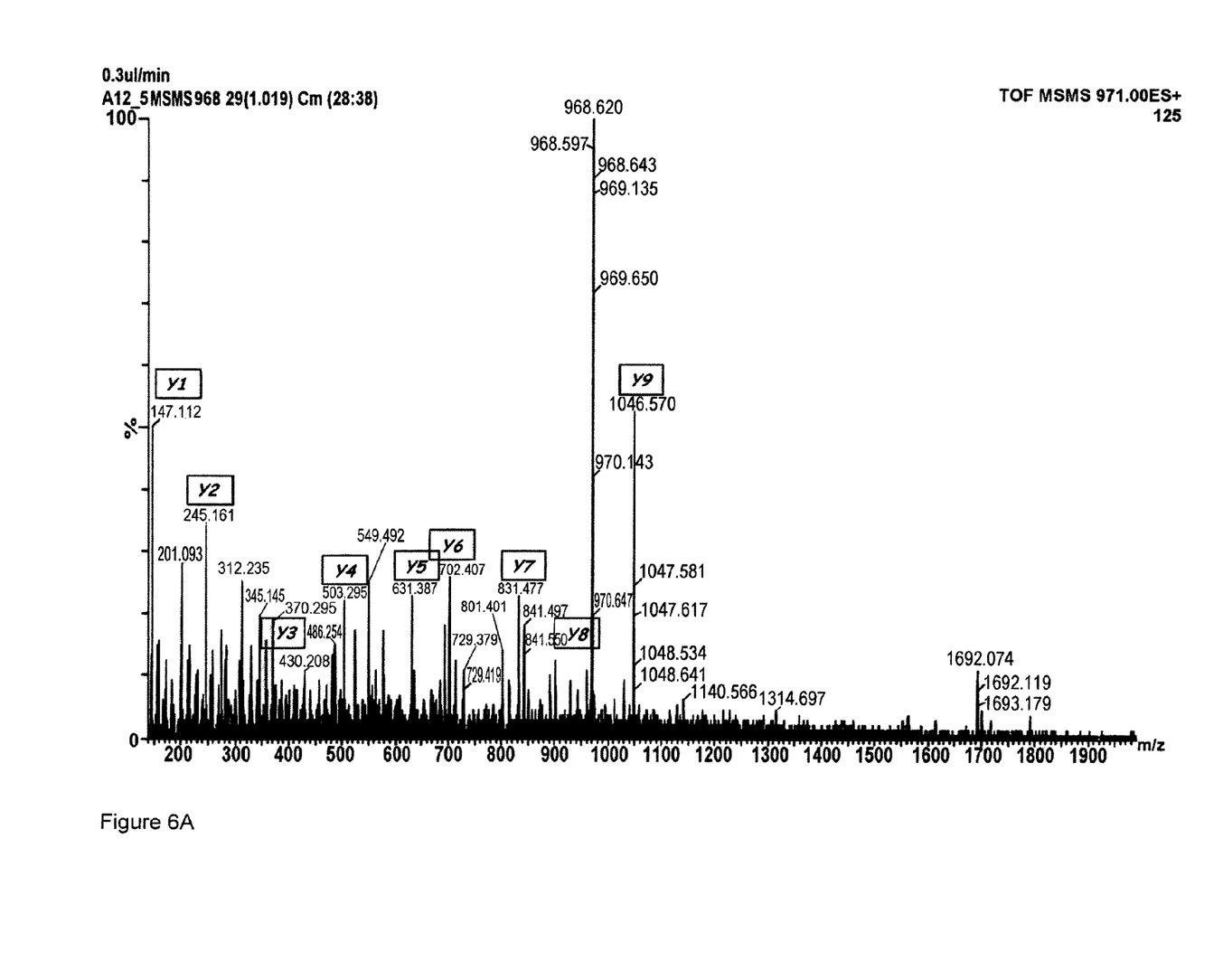
FIG. 6A is a LC/MS/MS graph showing the y-series ions of one Group B peak.
Figure 6B:
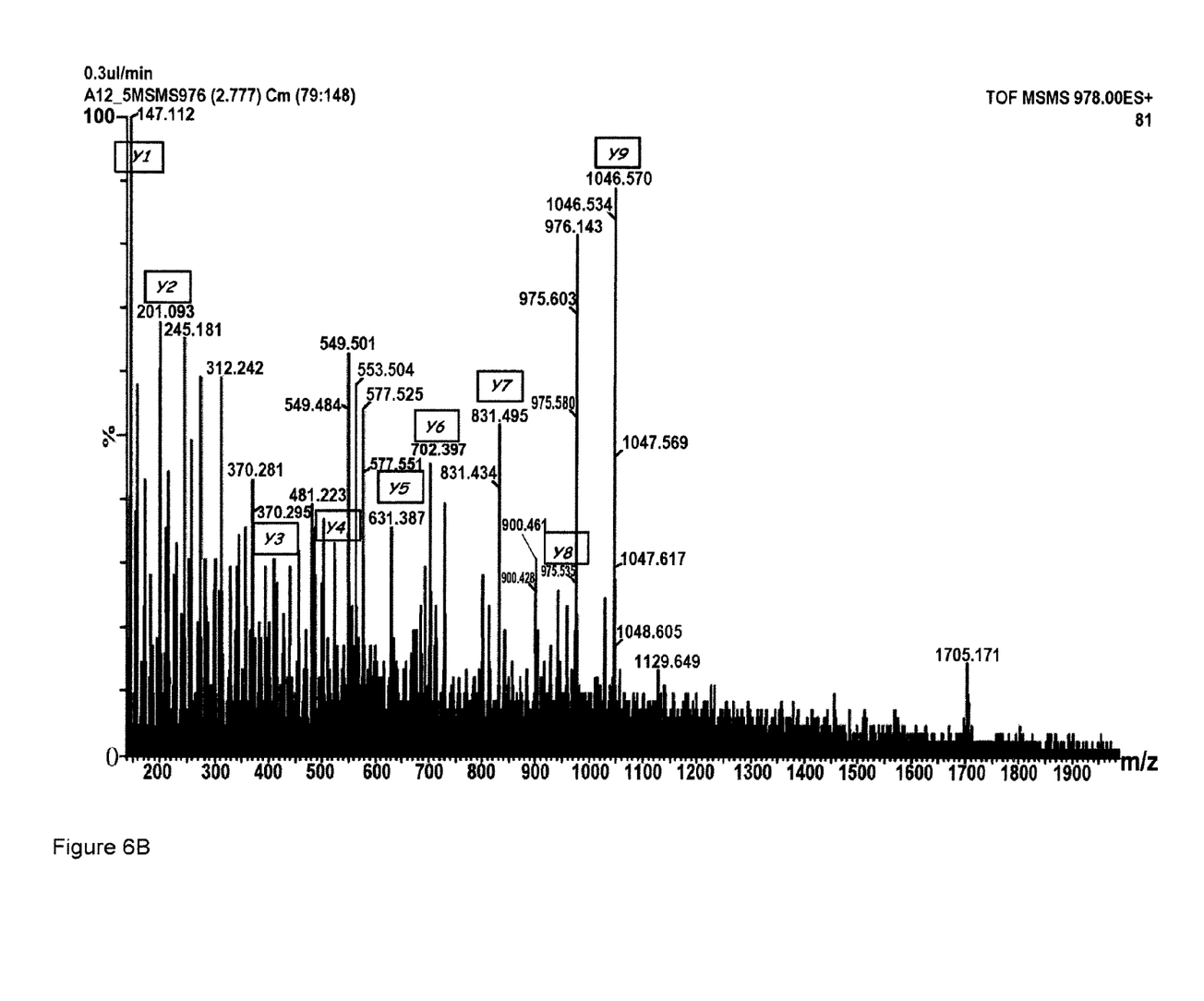
FIG. 6B is a LC/MS/MS graph showing the y-series ions of another Group B peak.

Based on the y-series ions in both peaks (see FIGS. 6A and 6B), it is determined that they represented two peptides having the same amino acid sequence, i.e., $C_{17}$SQEAKQEVK (SEQ ID NO:7). More specifically, the amino acid residues from y9 to y1 are SQEAKQEVK (SEQ ID NO:8) and the $C_{17}$ residue was not shown in the MS/MS mode, indicating that this residue was modified.

Taken together, all of results noted above show that the variations in the intact rAg473 protein resulted from various modifications at the $C_{17}$ residue, not from mutations in the protein's amino acid sequence.

Figure 5B:
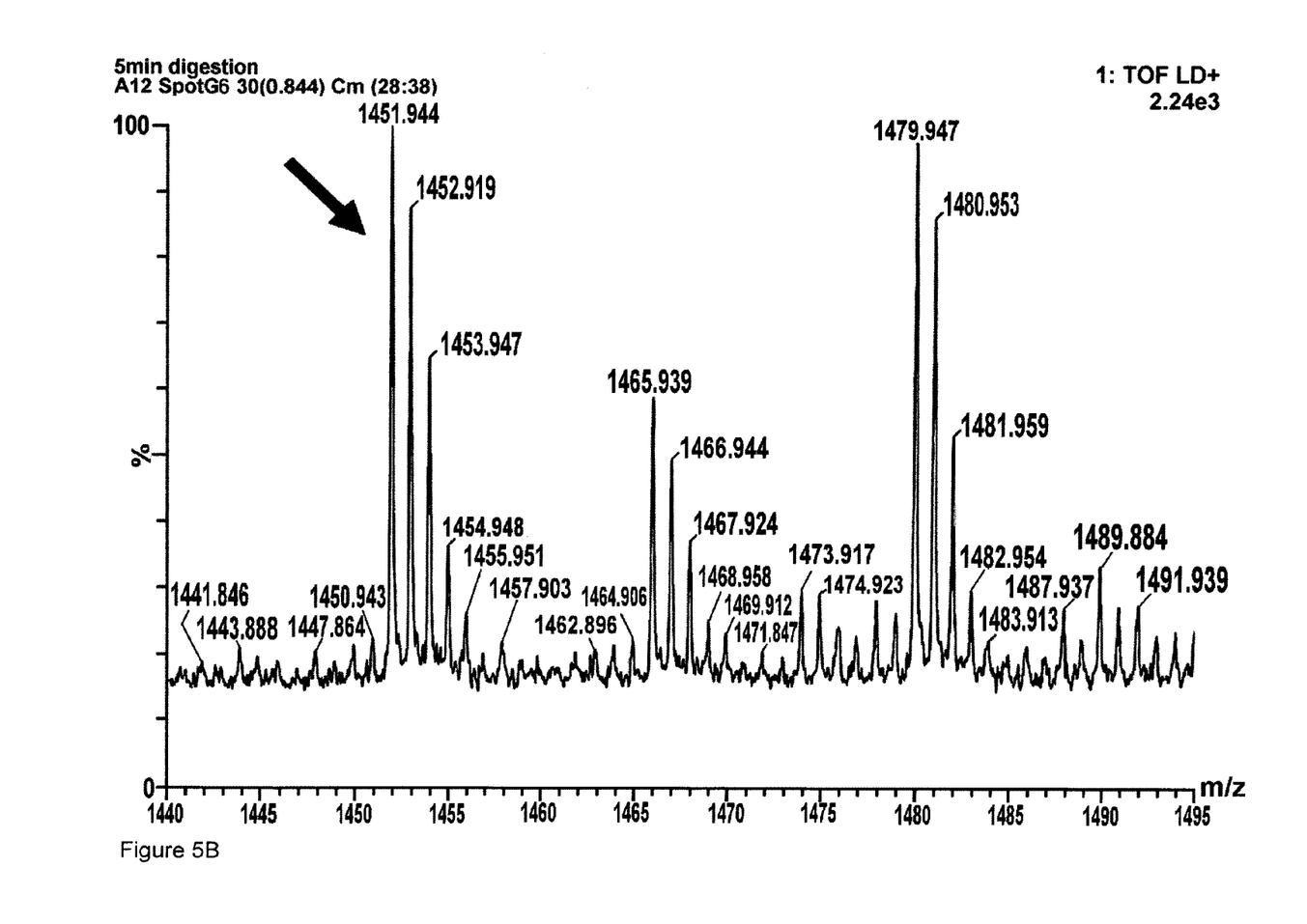
FIG. 5B is a MALDI-TOF MS graph of the Group A peaks, including peaks at m/z 1451.9, 1465.9, and 1479.9.
Figure 5C:
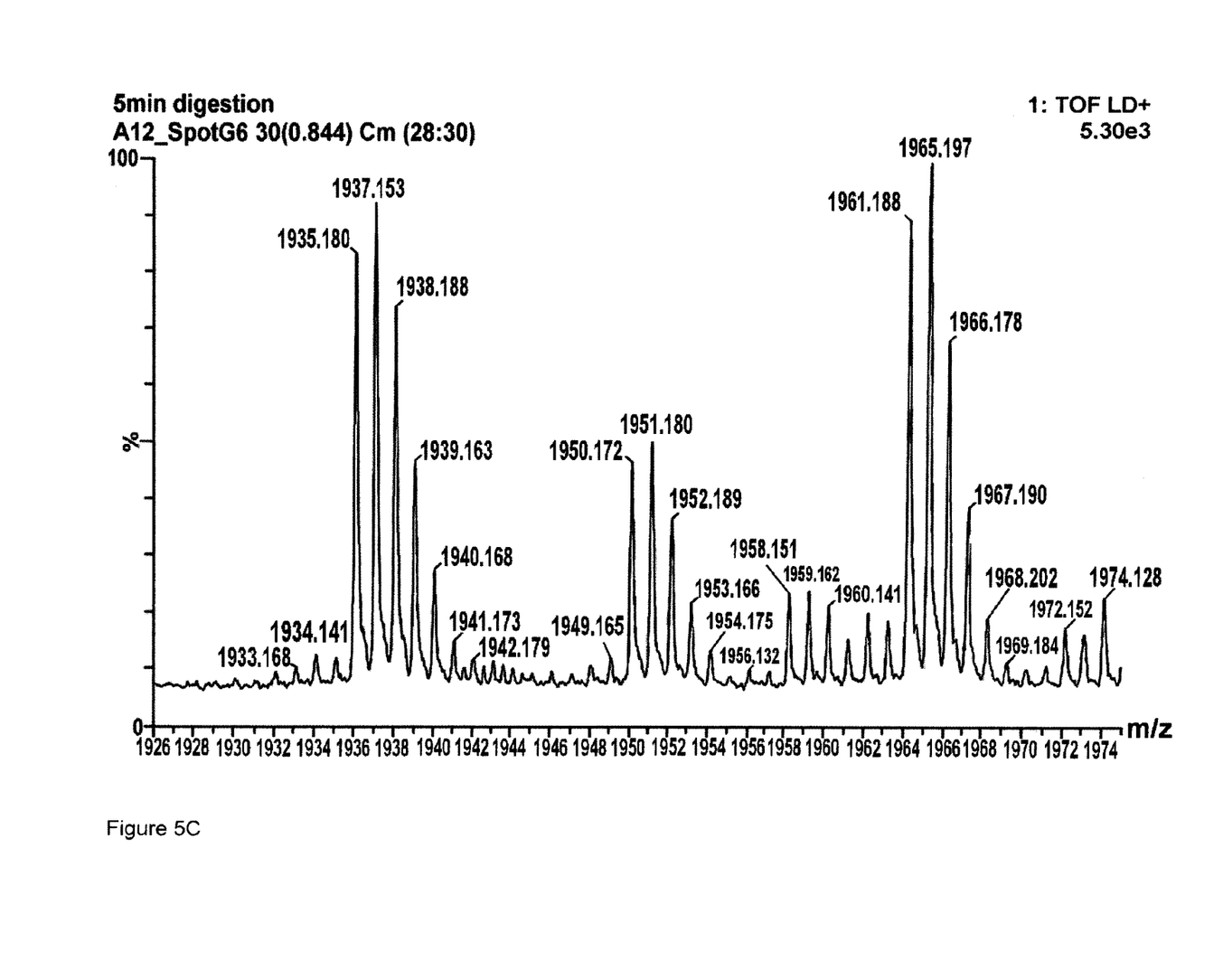
FIG. 5C is a MALDI-TOF MS graph of the Group B peaks, including the peaks at m/z 1936.2, 1950.2, and 1964.2.
Figure 7:
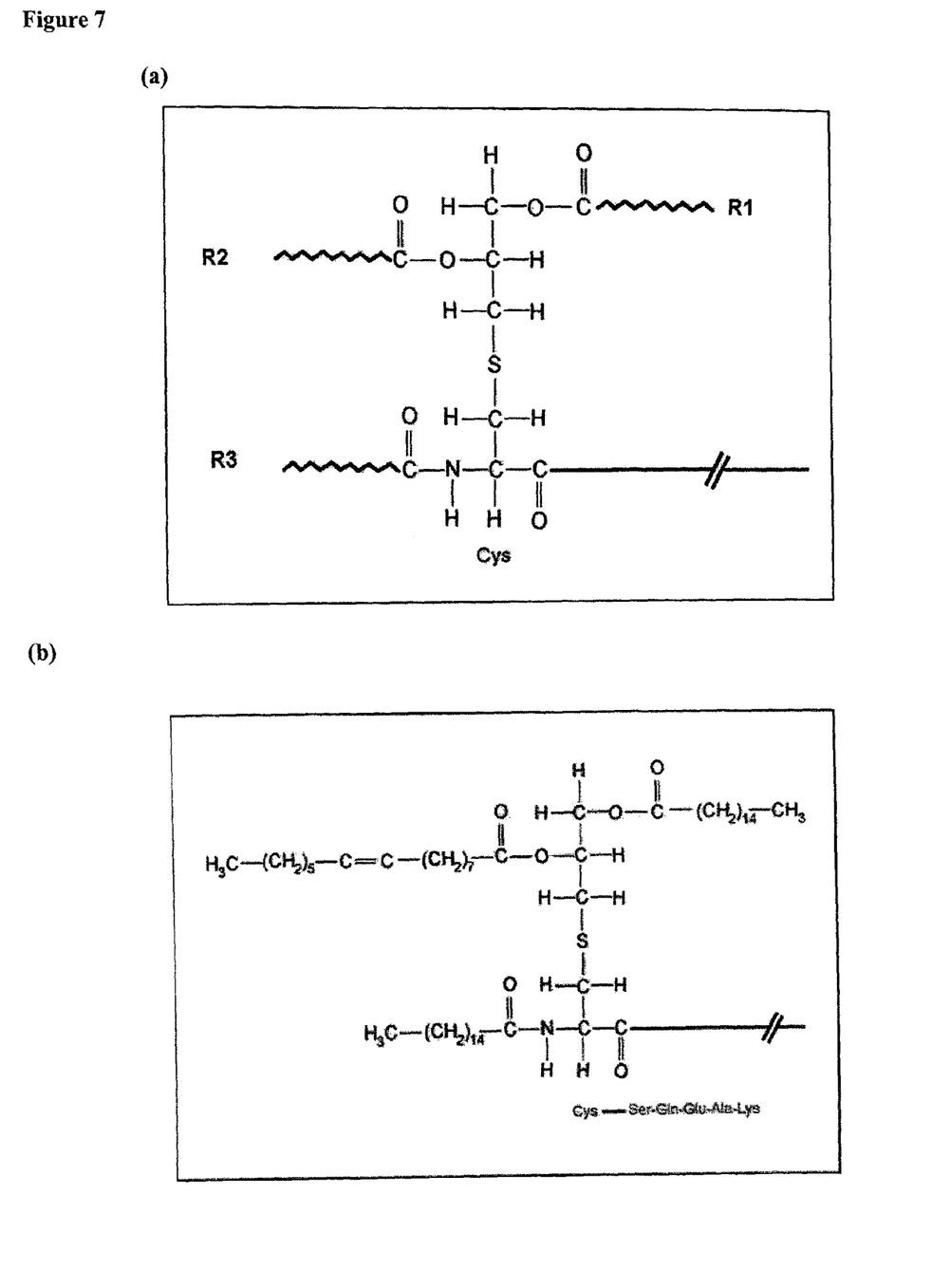
FIG. 7 a diagram showing structures of lipid moieties in E. coli lipoproteins. Panel (a): structure of a representative lipid moiety; Panel (b): deduced structure of a lipid moiety attached to the N-terminal of the rAg473 protein expressed in C43(DE3) (SEQ ID NO:9).

As Ag473 is a lipidated protein in its native state, it is likely that the rAg473 protein expressed in C43(DE3) was lipidated at the $C_{17}$ position. It is known that the lipid moieties of *E. coli* lipoproteins derive from a lipid phosphatidylglycerol (donor phosphatidylglycerol) in *E. coli* membrane. See Sankaran et al., J. Biol. Chem. 269:19701-19706 (1994). The acryl chains in phosphatidylglycerol molecules, saturated or unsaturated, usually include 16-20 carbon atoms. The structure of one exemplary phosphatidylglycerol is shown in FIG. 7A. In this structure, R1 is palmitate, R2 can be other types of fatty acids (see Cronon et al., Bacteriol Rev., 39:232-256, 1975; Raetz, Microbiol. Rev. 42:614-659, 1978; and Schlesinger, CRC Press, Boca Raton, pp 197, 1993), and R3 is the diacylglycerol group in the donor phosphatidylglycerol. The mass of this exemplary phosphatidylglycerol is 893.4 amu, as calculated based on this structure. The mass of the peak pointed to by the arrow in FIG. 5B, representing an N-terminal fragment of rAg473, is 895.4 amu. This result indicates that the N-terminal fragment is modified with a fatty acid molecule, attached to the $C_{17}$ residue, that includes a double bond in its acyl chain. Taken together, the structure of at least one lipid chain attached to the N-terminal fragment of rAg473 is N-palmitoyl-S-(1-palmitoyl-2-palmitoleoyl)-glyceryl-Cys-Ser-Gln-Glu-Ala-Lys (SEQ ID NO:9). See FIG. 7B.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of producing a lipidated protein in *E. coli*, comprising
providing a host *E. coli* cell transformed with an expression plasmid including a nucleotide sequence that encodes a naturally lipidated protein, wherein the host *E. coli* cell is C41 (DE3), C43 (DE3), DK8 (DE3)S, or C2014 (DE3); and the naturally lipidated protein has the amino acid sequence of SEQ ID NO: 1, and
culturing the host *E. coli* cell to express the naturally lipidated protein in lipidated form.

2. The method of claim 1, wherein the host *E. coli* cell is C41 (DE3).

3. The method of claim 1, wherein the host *E. coli* cell is C43 (DE3).

4. The method of claim 1, further comprising, after the culturing step, isolating the naturally lipidated protein in lipidated form and confirming that the expressed protein is lipidated.

5. The method of claim 4, wherein the host *E. coli* cell is C41 (DE3).

6. The method of claim 4, wherein the host *E. coli* cell is C43 (DE3).

* * * * *